United States Patent [19]

Marks et al.

[11] Patent Number: 5,110,948
[45] Date of Patent: May 5, 1992

[54] ORGANOSAMARIUM CATALYSTS FOR THE HYDROAMINATION OF OLEFINS

[75] Inventors: Tobin J. Marks; Steven P. Nolan, both of Evanston; Michel R. Gagne, Chicago, all of Ill.

[73] Assignee: Northwestern University, Evanston, Ill.

[21] Appl. No.: 492,823

[22] Filed: Mar. 13, 1990

Related U.S. Application Data

[63] Continuation-in-part of Ser. No. 291,186, Dec. 28, 1988, abandoned.

[51] Int. Cl.$^5$ .............. C07D 207/06; C07D 295/023; C07D 24/02; C07D 209/04
[52] U.S. Cl. .................................. 548/579; 546/184; 564/485; 548/485
[58] Field of Search ............... 548/579, 580; 546/184; 564/485; 502/152, 153

[56] References Cited

U.S. PATENT DOCUMENTS

| | | | |
|---|---|---|---|
| Re. 29,368 | 8/1977 | Pez | 260/429.3 |
| 2,831,880 | 4/1958 | Benkeser | 260/439 |
| 3,060,215 | 10/1962 | Rosenberg et al. | 260/439 |
| 3,849,459 | 11/1974 | Maitlis et al. | 260/429 CY |
| 3,969,386 | 7/1976 | Ballard et al. | 260/429 R |
| 4,423,276 | 12/1983 | Johnson | 585/665 |
| 4,454,321 | 1/1984 | Gardner et al. | 546/184 |
| 4,665,046 | 5/1987 | Campbell, Jr. | 502/102 |
| 4,668,773 | 5/1987 | Marks et al. | 534/15 |
| 4,716,257 | 12/1987 | Marks et al. | 585/275 |
| 4,801,666 | 1/1989 | Marks et al. | 526/123 |

OTHER PUBLICATIONS

Ambuehl et al., *Journal of Organo Metallic Chemistry*, 160 (1978) pp. 329-335.
Pez et al., *Pure and Applied Chemistry*, 57 No. 12, (1985), pp. 1917-1926.
Evans et al., "Organolanthanide Hydride Chemistry, etc.", *J. Am. Chem. Soc.* (1983), 105, pp. 1401-1403.
Jeske et al., "Highly Reactive Organolanthanides, etc.", *J. Am. Chem. Soc.*, (1985), 107, 8111-8118.
Watson et al., "Homogeneous Leanthanide Compleses as Polymerization and Oligomerization Catalysts: Mechanistic Studies," ACS Symposium Series, 1983, 212, 459-479.
Watson and Parshall, "Organolanthanides in Catalysts," Acc. Chem. Res., 1985, 18, 51-56.
Mauermann, Sweptson, and Marks, "5f$^3$ vs. 4f$^3$". Routes to and Properties of Highly Reactive Neodymium (III) Hydrocarbyl and Hydride Complexes, Organometallics, 4, 200 (1985).
Jeske, Schock, Swepton, Schumann, and Marks, "Highly Reactive Organolanthanides. Synthesis, Chemistry, and Structures of 4f Hydrocarbyls and Hydrides with Chelating Bis (Polymethylcyclopentadienyl) Ligands," J. Am. Chem. Soc., 1985, 107, 8103-8110.
Jeske, Lauke, Mauermann, Schumann, and Marks, "Highly Reactive Organolanthanides. Systematic Routes to and Olefin Chemistry of Early and Late Bis (pentamethylcyclopentadienyl) 4f Hyudrocarbyl and Hydride Complexes," J. Am. Chem. Soc. 1985, 107, 8091-8103.
Deeba, et al., "Direct Amination of Ethylene by Zeolite Catalysis," J. Chem. Soc. Chem. Commun. 1987, 562-563.
Evans, William J., "Polyhedron Report No. 20: The Organometallic Chemistry of the Lanthanide Elements in Low Oxidation States," Polyhedron, 1987, vol. 6, No. 5, 803-835.

(List continued on next page.)

*Primary Examiner*—Richard L. Raymond
*Assistant Examiner*—Peter G. O'Sullivan
*Attorney, Agent, or Firm*—Welsh & Katz, Ltd.

[57] ABSTRACT

The reaction of a samarium catalyst [$\eta^5$—(CH$_3$)$_5$C$_5$]$_2$Sm(THF)$_2$ with amino-olefins provides a straightforward route to a heterocyclic compound. Alternatively, the reaction of olefins with the samarium catalyst in the presence of an amine results in an aminoalkane.

21 Claims, 1 Drawing Sheet

OTHER PUBLICATIONS

Finke et al., "Organolanthanide and Organoactinide Additions Exhibiting Enhanced Reactivity. 4. Products Stoichiometry, and Preliminary Kinetic Studies of the Reaction of $(C_5Me_5)_2Sm^{II}OEt_2$ and $(C_5Me_5)_2Eu^{II}OEt_2$ with Alkyl and Aryl Halides. Evidence of Importance of Electron Transfer in Atom-Abstraction Oxidative Additions," Organometallics, 1987, 6, 1356-1358.

Megedus, et al., "Palladium-Assisted Amination of Olefins. A mechanistic Study," J. Am. Chem. Soc. 1984, 106, 7122-7126.

Surzur et al., "Bicyclisations Radicalaires Des N-Chloroamines Ethyleniques," Tetrahedron Letter, 1974, No. 25, 2191-2194.

Fagan et al., "Insertion of Carbon Monoxide into Metal-Nitrogen Bonds. Synthesis, Chemistry, Structures, and Structural Dynamics of Bis (pentamethylcyclopentadienyl) Organoactinide Dialkylamides and $n^2$-Carbamoyls", J. Am. Chem. Soc., 1981, 103, 2206-2220.

Tamaru et al., "Urea as the Most Reactive and Versatile Nitrogen Nucleophile for the Palladium (2+)-Catalyzed Cyclization of Unsaturated Amines," J. Am. Chem. Soc., 1988, 110, 3994-4002.

Pugin et al., "Palladium-Promoted Cyclization Reactions of Aminoalkenes," Journal of Organometallic Chemistry, 1981, 214, 125-133.

Gasc et al., "Tetrahedron Report No. 144: Amination al Alkenes," Tetrahedron, 1983, vol. 39, No. 5, 703-731.

Deeba et al., "Heterogeneous Acid-Catalyzed Amination of Isobutene to tert-Butylamine," J. Org. Chem. 1988, 53, 4594-4596.

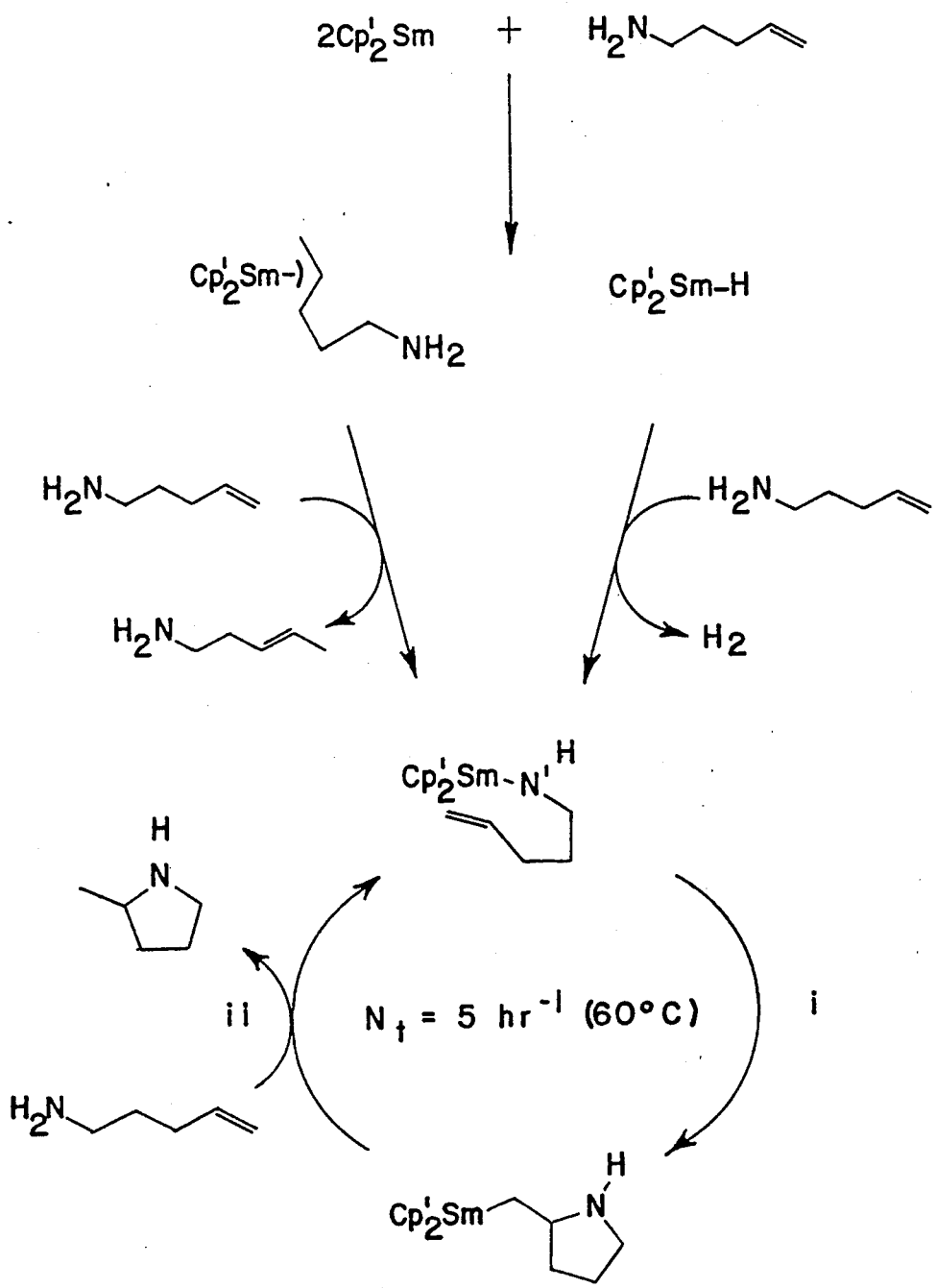

ORGANOSAMARIUM CATALYSTS FOR THE HYDROAMINATION OF OLEFINS

This application is a continuation-in-part of application Ser. No. 291,186, filed Dec. 28, 1988, now abandoned, by Marks and Gagne, entitled "Method for Hydroaminating Olefins."

This application relates to catalysts and more particularly to a method for the hydroamination of olefins through the use of organosamarium catalysts.

BACKGROUND OF THE INVENTION

The catalytic addition of N-H bonds to olefins (eq.(I)) to yield amines is a process of potentially great technological importance.

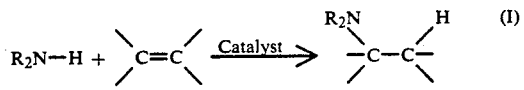

However, presently known catalyst systems, employing palladium, platinum, or alkali metal catalysts, can be relatively inefficient, having very low rates, poor catalyst lifetimes, poor selectivities, or requiring initial modification of the amine—e.g., tosylation. As a result, many current catalytic processes involve the conversion of alcohols to amines with the alcohol, which in turn, is prepared from the olefin. Such hydroamination reactions are exothermic, yet thus far have proven difficult to perform due to a lack of suitable catalysts and, to a lesser extent, unfavorable entropy effects. As a result, more attention has been paid to aminating olefins intramolecularly, and limited successes have been experienced in both stoichiometric and catalytic type reactions. A rapid efficient, direct process for the hydroamination of olefins would be beneficial.

Organolanthanide catalysts have been found useful as noted in U.S. Pat. No. 4,668,773 to Marks and Mauermann, the organolanthanide complexes $[\eta^5-(CH_3)_5C_5]_2MCl_2-Li](C_2H_5)_2O]_2^+$, M=La, Nd, Sm, Lu, with $LiCH[Si(CH_3)_3]_3$ were shown to provide a straight-forward route to ether-free and halide-free bis(pentamethylcyclopentadienyl) lanthanide alkyls $[\eta^5(CH_3)_5C_5]_2MCH[Si(CH_3)_3]_2$. Such $[\eta^5(CH_3)_5C_5]_2MCH[Si(CH_3)_3]_2$ complexes react with H: under mild conditions to yield the corresponding hydrides $[\eta^5(CH_3)_5(C_5)_2MH]_2$. These complexes have been found to be extremely active homogeneous olefin polymerization catalysts, as well as catalysts for olefin and acetylene hydrogenation.

SUMMARY OF THE INVENTION

Therefore, an object of the subject invention is the use of organolanthanide catalysts for use in hydroamination reactions.

Another object of the subject invention is a shelf-stable environmentally acceptable organolanthanide catalyst and its use in a method for the hydroamination of olefins.

A further object of the subject application is a method for the synthesis of an organosamarium catalyst and the use of the organosamarium catalyst to hydroaminate amino-olefins.

These and other objects are attained in accordance with the subject invention wherein $Cp'_2Sm(THF)_2$ and $Cp'_2Sm$ ($Cp'=\eta^5-R_5C_5$, R=H, an alkyl or aryl group or any mixture thereof; THF=tetrahydrofuran), and more particularly bis(pentamethylcyclopentadienyl) samarium bis(tetrahydrofuran) are prepared as effective catalyst precursors for the hydroamination of olefins. The procedure of the subject invention comprises the oxidative addition of the amino-olefin to the catalyst, forming in the process one equivalent of samarium-allyl and one equivalent of samarium-hydride. These equivalents can further react in a second step with the amino-olefin to yield the catalytically active, known samarium-amido species. This species further reacts, via an olefin insertion, into Sm—N bond and a protonation step to yield the cyclized amine and to regenerate the active catalyst. $Cp'_2Sm(THF)_2$ and its related entity $Cp'_2Sm$ have the distinct advantage of not only being an efficient catalytic agent, but also they are extremely easily prepared.

These and other objects of the subject invention, together with additional features contributing thereto and advantages occurring therefore will be apparent from the following description of one embodiment of the invention when read in conjunction with the accompanying drawing wherein:

The figure is a representation of the reaction pathway of the method of the subject invention.

DETAILED DESCRIPTION OF THE INVENTION

All operations were performed with rigorous exclusion of oxygen and moisture in flamed Schlenk-type glassware in a dual manifold Schlenk line or interfaced to a high vacuum ($10^{-5}$ torr) system, or in a nitrogen or argon filled glovebox with a high capacity atmosphere recirculator. Argon, ethylene, propylene, dihydrogen, and deuterium gas were purified by passage through a supported MnO oxygen removal column and a molecular sieve column. Aliphatic hydrocarbon solvents were pretreated with concentrated $H_2SO_4$, $KMnO_4$ solution, $MgSO_4$, and Na, 4Å molecular sieves. All reaction solvents were distilled from Na/K/benzophenone under nitrogen and were condensed and stored in vacuo in bulbs on the vacuum line containing a small amount of $[Ti(\eta^5-C_5H_5)_2Cl]_2ZnCl_2$ as indicator. Cyclohexane and heptane were additionally vacuum transferred onto Na/K and stirred for at least a day before use in catalytic experiments. The olefins, all hexenes and cyclohexene, were purified by stirring over Na/K for at least 6 hours and were freshly vacuum transferred. The amines were purified by stirring over Na/K for ½ hour, followed by at least 3 successive vacuum transfers onto freshly activated 4Å molecular sieves (at least 1 day each); and freshly vacuum transferred before use. Deuterated solvents were dried over Na/K and vacuum transferred before use. Pentamethylcyclopentadiene was prepared by the procedure set forth in *Oroanometallics.* 1984, 3, 819–821.

I. Catalyst Syntheses

In general, the $Cp'_2Sm(THF)_2$ complex may be prepared in one simple step.

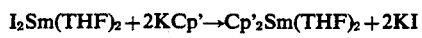

II. Hydroamination

The anaerobic catalytic reaction of $Cp'_2Sm(THF)_2$ with a variety of dry, degassed amino olefins and alkenes (typically in 100–200-fold stoichiometric excess)

proceeds to completion in hydrocarbon solvents such as benzene, toluene, cyclohexane, or pentane. The base-free adduct Cp'$_2$Sm may also be used as a catalyst with no significant difference in cyclization rates. The reactions may be conveniently monitored by NMR spectroscopy and the products may be identified by comparison with spectral data from the literature and/or with those of authentic samples.

By supplying olefins to the Sm—N bond intramolecularly in an organosamarium compound, it is possible to have a large effective concentration of olefin around the amine, while at the same time reducing the disfavoring entropic factor referred to above when the reaction is performed intermolecularly.

A. Synthesis of Heterocycles

To investigate one aspect of olefin hydroamination and in furtherance of one embodiment of the subject invention, a variety of cyclized amines may be synthesized from amino olefins, as set forth in Examples 1 through 6 below when reacted with catalytic amounts of an organosamarium catalyst, Cp'$_2$Sm(THF)$_2$. The catalyst Cp'$_2$Sm(THF)$_2$ readily combines with olefins in a first step, thereby forming the expected organosamarium-allyl-complexes. The amido complexes all have the ability to intramolecularly insert an olefin into the resulting samarium-NHR bond. The insertion results in an alkyl complex which, in the presence of excess amine, is rapidly protonated, yielding an alkane, and reforming an amido compound. The combination of all the reactions set forth in the figure constitutes a catalytic cycle which demonstrates the key steps believed to be involved in forming a group of heterocyclic compounds.

The following examples demonstrate the versatility of the catalyst of the subject invention, showing the use of alkyl (Examples 1–8) aryl (Example 9) and hydrogen (Example 10) in Cp', as well as the use of Cp$_2$Sm (Examples 7–8).

EXAMPLE 1

30 mg of [$\eta^5$(CH$_3$)$_5$C$_5$]$_2$Sm in toluene was heated with 100 equivalents (350 mg) of 1-amino-4-pentene at 60° C. in a closed vessel under an inert atmosphere. After 2 days the reaction mixture was allowed to cool to room temperature and the volatiles were vacuum transferred into a second container. Analysis of the volatiles by standard analytical techniques give a determination of greater than 97% conversion to 2-methylpyrrolidine.

TABLE I

| Example | Starting Amine | Product | Catalyst* |
|---|---|---|---|
| 1 | H$_2$N–CH$_2$CH$_2$CH$_2$CH=CH$_2$ | 2-methylpyrrolidine | Cp'$_2$Sm(THF)$_2$ |
| 2 | H$_2$N–CH$_2$CH$_2$CH$_2$CH$_2$CH=CH$_2$ | 2-methylpiperidine | Cp'$_2$Sm(THF)$_2$ |
| 3 | H$_2$N–C(CH$_3$)$_2$CH$_2$CH=CH$_2$ | 2,4,4-trimethylpyrrolidine | Cp'$_2$Sm(THF)$_2$ |
| 4 | CH$_3$CH(NH$_2$)CH$_2$CH$_2$CH=CH$_2$ | 2,5-dimethylpyrrolidine | Cp'$_2$Sm(THF)$_2$ |
| 5 | MeNH–CH$_2$CH$_2$CH$_2$CH=CH$_2$ | 1,2-dimethylpyrrolidine | Cp'$_2$Sm(THF)$_2$ |
| 6 | 2-allylaniline | 2-methylindoline | Cp'$_2$Sm(THF)$_2$ |
| 7 | H$_2$N–CH$_2$CH$_2$CH$_2$CH=CH$_2$ | 2-methylpyrrolidine | Cp'$_2$Sm |

TABLE I-continued

| Example | Starting Amine | Product | Catalyst* |
|---|---|---|---|
| 8 | 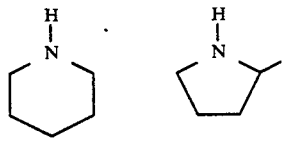 + NH₃ | NH₂ /\/\/\ | Cp'₂Sm |

*Cp' = η⁵(CH₃)₅C₅

EXAMPLE 9

30 mg of bis(pentabenzylcyclopentadienyl) samarium (II) bis(tetrahydrofuran) (CpΔ₂Sm(THF)₂) in toluene is heated with 100 equivalents of 1-amino-4-pentene at 60° C. in a closed vessel under an inert atmosphere. After two days the reaction mixture is allowed to cool to room temperature and the volatiles are vacuum transferred into a second container. 2-methylpyrrolidine is the resulting product.

EXAMPLE 10

30 mg of bis(cyclopentadienyl) samarium (II) bis(tetrahydrofuran) ((C₅H₅)₂Sm(THF)₂ or Cp'''₂Sm(THF)₂) in toluene is heated with 100 equivalents of 1-amino-4-pentene at 60° C. in a closed vessel under an inert atmosphere. After two days the reaction mixture is allowed to cool to room temperature and the volatiles are vacuum transferred into a second container. 2-methylpyrrolidine is the resulting product.

By varying the amine one can also see a number of points, the most noticeable being the region specificity of the cyclizations. In each case, it is possible to insert the olefin in one of two orientations, hypothetically yielding the following structures with 1-amino-4-pentene as the amine:

However, as is the case with 1-amino-4-pentene, and with the other amines, the smaller of the two possible ring sizes corresponding to lower ring strain in the transition state appears to be favored with no indication of side products.

As set forth above, 5-membered rings (e.g., Example 2) are formed much more readily than the corresponding 6-membered rings. The fact that six membered rints can be formed at all is noteworthy since this does not occur readily if at all with other catalytic systems.

By studying the kinetics of this process, one sees that the rate of appearance of cyclized product and hence the disappearance of he starting amine is linear with time, indicating zero order kinetics in the substrate. In the catalytic cycle, there are only two steps involved in the process, and since it is known that amine protonolysis of lanthanide-alkyls is rapid, the rate determining step should be the olefin-insertion into the lanthanide-N bond, indicating a sterically controlled process.

EXAMPLE 11

Cp'₂Sm is prepared from Cp'₂Sm(THF)₂ by vacuum sublimation. 30 mg of Cp'₂Sm in toluene was heated with 100 equivalents (350 mg) of 1-amino-4-pentene at 60° C. in a closed vessel under an inert atmosphere. After 2 days the reaction mixture was allowed to cool to room temperature and the volatiles were vacuum transferred into a second container. Analysis of the volatiles by standard analytical techniques showed greater than 97% conversion to 2-metylpyrrolidien.

B. Synthesis of Aminolakanes

In addition to synthesizing heterocycles through hydroamination, olefins, such as ethylene, propylene, butadiene, 1-butene, 1-hexene, 1,5hexadine, 1-heptene, and the like, can be hydroaminated with ammonia or other primary and secondary amines, such as RΔNH₂, RΔ₂NH, where RΔ can be an alkyl or aryl group. Hydroamination can be effected by stirring solutions of Cp'₂Sm or Cp'₂Sm (THF)₂ with the olefin under an ammonia atmosphere at various pressures. CpΔSm(THF)₂ or Cp'''Sm(THF)₂ may also be used. It is believed that most olefins an be hydroaminated provided that steric considerations are favorable and do not substantially impede the progress o the reaction. The solvents involved are as before. This process presumably involves ammonia or Ln—NH₂ at the insertion step, dependent on the amine source.

EXAMPLE 12

20 mg (48 μmol) of Cp'₂Sm is added to a reaction flask under a nitrogen atmosphere. The flask is connected to a high vacuum line and evacuated. 1-hexene which has been rigorously dried and degassed is then vacuum transferred onto the catalyst with stirring, the solution is then put under an atmosphere of ammonia. The reaction is monitored by the ammonia uptake. Once ammonia uptake has ceased, the solution is degassed, and the contents are then vacuum transferred to a second vessel. The result is 2-amino-hexane.

In general, it should be noted that the overall catalytic mechanism is sensitive to Lewis bases and Bronsted acids. Therefore, if hydroamination of materials that contain alcohols, thiols, carboxylic acids, for the like is required, protecting groups may be needed and can therefore be added as known in the art to inhibit the effect the interfering groups may have.

C. Heterogeneous Catalysis

In addition to the homogeneous catalytic synthetic methods described above, heterogeneous catalytic synthesis methods are envisioned as being within the cope of the subject invention as well. In such a heterogeneous process, the organolanthanide catalyst would be absorbed on the surface o the suitable inorganic substrate such as silica, silica gel, alumina, magnesium chloride, magnesium oxide or the like, and placed in contact with the reactants.

While the invention has been described switch reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A method for hydroaminating an amino-olefin,, comprising contacting said amino-olefin with a catalyst under an inert atmosphere, said catalyst being selected from the group consisting of Cp'$_2$Sm(THF)$_2$ and Cp'$_2$Sm, where Cp'=$\eta_5$R$_5$C$_5$, and R is selected from the group consisting of H, alkyl or aryl.

2. A method for hydroaminating an olefin to yield an amino alkane comprising contacting said olefin with a catalyst in the presence of an amine or under an ammonia atmosphere, said catalyst having a formula selected from the group consisting of Cp'$_2$Sm(THF)$_2$ and Cp'$_2$Sm, wherein Cp'=$\eta^5$R$_5$C$_5$, R being selected from the group consisting of hydrogen, alkyl groups, and aryl groups.

3. The method of claim 2 wherein said amine is NH$_3$.

4. The method of claim 1 wherein said amino-olefin is selected from the group consisting of:

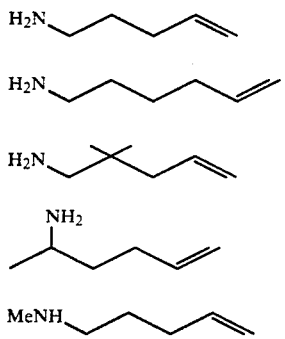

5. The method of claim 2 wherein said catalyst is in a solvent selected from the group consisting of tetrahydrofuran, cyclohexane, toluene, benzene, and pentane.

6. The method of claim 2 wherein said catalyst is homogeneous.

7. The method of claim 2 wherein said catalyst is heterogeneous.

8. The method of claim 7 wherein said catalyst is adsorbed on an inorganic substrate selected from the group consisting of silica, silica gel, alumina, magnesium chloride, and magnesium oxide.

9. A method for hydroaminating an unsaturated monomer selected from the group consisting of amino-olefins and amino cyclic alkenes comprising the steps of dissolving said unsaturated monomer in a solvent with a catalyst selected from the group consisting of Cp'$_2$Sm(THF)$_2$ and Cp'$_2$Sm under an inert atmosphere, wherein Cp'=$\eta^5$R$_5$C$_5$, R being selected from the group consisting of hydrogen, alkyl groups, and aryl groups.

10. The method of claim 9 wherein said solvent is toluene.

11. The method of claim 9 wherein said unsaturated monomer is selected from the group consisting of:

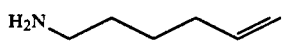

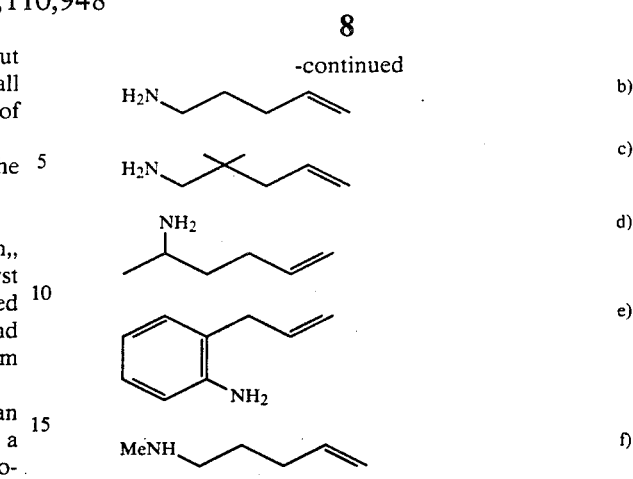

12. A method of claim 9 wherein said solvent is selected from the group consisting of aliphatic hydrocarbons, aromatic hydrocarbons, and mixtures thereof.

13. A method of hydroaminating an amino-olefin, comprising the steps of$_2$
   (a) evacuating a reaction vessel;
   (b) adding a solvent to said reaction vessel;
   (c) adding a solution containing a catalyst selected from the group consisting of Cp'$_2$Sm(THF)$_2$ and Cp'$_2$Sm , wherein Cp'=$\eta^5$R$_5$C$_5$, R being selected from the group consisting of hydrogen, alkyl groups, and aryl groups, to said reaction vessel;
   (d) maintaining pressure with an atmosphere selected from argon or nitrogen in said reaction vessel at approximately one atmosphere;
   (e) stirring the solvent and catalyst solution rapidly for several minutes;
   (f) transferring an amino-olefin to said mixture; and
   (g) heating the reaction vessel, whereby the amino-olefin forms into a cyclic compound which may be isolated.

14. The method of claim 13 wherein said catalyst solution has a solvent selected from the group consisting of tetrahydrofuran, cyclohexane, toluene, benzene, and pentane.

15. The method of claim 13 wherein said catalyst is homogeneous.

16. The method of claim 13 wherein said catalyst is heterogeneous.

17. The method of claim 16 wherein said catalyst is adsorbed on an inorganic substrate selected from the group consisting of silica, silica gel, alumina, magnesium chloride, and magnesium oxide.

18. A method for hydroaminating an unsaturated monomer selected from the group consisting of α-olefins and cycloalkenes comprising the steps of dissolving said unsaturated monomer in a solvent and contacting said olefin solution with a catalyst selected from the group consisting of Cp'$_2$Sm(THF)$_2$ and Cp'$_2$Sm, wherein Cp'=$\eta^5$R$_5$C$_5$, R being selected rom the group consisting of hydrogen, alkyl groups, and aryl groups.

19. The method of claim 18 wherein said solvent is selected from the group consisting of aliphatic hydrocarbons, aromatic hydrocarbons, and mixtures thereof.

20. The method of claim 18 wherein said solvent is toluene.

21. The method of claim 18 wherein said unsaturated monomer is selected from the group consisting of ethylene, propylene, 1-butene, butadiene, 1-hexene, 1,5-hexadiene, and 1-heptene.

* * * * *

UNITED STATES PATENT AND TRADEMARK OFFICE
CERTIFICATE OF CORRECTION

PATENT NO. : No. 5,110,948
DATED : May 5, 1992
INVENTOR(S) : Marks, et al.

It is certified that error appears in the above-identified patent and that said Letters Patent is hereby corrected as shown below:

Column 1, Line 48, "H:" should be --$H_2$--.

Column 2, Lines 10-11, delete "-" which appears between "samarium-amido species".

Column 2, Line 55, "*Oroanomet-*" should be -- *Organomet-* --.

Column 4, Line 18, delete "." which follows: "60°C."

Column 5, Line 10, "(Cp$\Delta_2$Sm(THF)$_2$" should --(Cp"$_2$Sm(THF)$_2$)--.

Column 5, Line 12, delete "." which follows "C."

Column 5, Line 22, delete "." which follows "60°C."

Column 5, Line 28, "region-specificity" should be --regiospecificity--.

Column 5, Line 48, "rints" should be --rings--.

Column 6, Line 10, "2-metylpyrrolidien" should be --2-metylpyrrolidine--.

UNITED STATES PATENT AND TRADEMARK OFFICE
CERTIFICATE OF CORRECTION

PATENT NO. : No. 5,110,948
DATED : May 5, 1992
INVENTOR(S) : Marks, et al.

It is certified that error appears in the above-identified patent and that said Letters Patent is hereby corrected as shown below:

Column 6, Lines 17-22, replace "Δ" with --"--, all occurrences.

Column 6, Line 25, "o the reaction" should be --of the reaction--.

Column 6, Line 43, insert --¨-- above "e" in "Bronsted acids".

Column 6, Line 55, "surface o the" should be --surface of a--.

Column 6, Line 60, "switch" should be --with--.

Column 7, Line 55, "cyclic alkenes" should be --cycloalkenes--.

Column 8, Line 22, "steps of$_2$" should be --steps of:--.

Column 8, Line 57, "selected rom" should be --selected from--.

Signed and Sealed this

Seventh Day of September, 1993

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,110,948

DATED : May 5, 1992

INVENTOR(S) : Marks, et al.

It is certified that error appears in the above-identified patent and that said Letters Patent is hereby corrected as shown below:

Column 1, between lines 8-9 insert the following new first paragraph:

--This invention was made with Government support under Grant No. F614 awarded by the National Science Foundation. The Government has certain rights in the invention.--

Signed and Sealed this

Twenty-sixth Day of October, 1993

Attest:

BRUCE LEHMAN

*Attesting Officer*   *Commissioner of Patents and Trademarks*